United States Patent
Nguyen et al.

(10) Patent No.: US 7,494,822 B2
(45) Date of Patent: Feb. 24, 2009

(54) METHOD OF QUANTIFICATION OF CARBOXYLIC ACIDS BY MASS SPECTROMETRY

(76) Inventors: Hoa D. Nguyen, 7735 E. Fieldcrest La., Orange, CA (US) 92869; Trinh D. Nguyen, 2077 Sprague #1, Anaheim, CA (US) 92802; Duc T. Nguyen, 14701 Bowling Green St., Westminster, CA (US) 92683

( * ) Notice: Subject to any disclaimer, the term of this patent is extended or adjusted under 35 U.S.C. 154(b) by 850 days.

(21) Appl. No.: 10/675,764

(22) Filed: Sep. 30, 2003

(65) Prior Publication Data

US 2005/0070023 A1  Mar. 31, 2005

(51) Int. Cl.
*G01N 24/00* (2006.01)
*G01N 33/00* (2006.01)

(52) U.S. Cl. ........................ 436/173; 436/129
(58) Field of Classification Search .................. None
See application file for complete search history.

(56) References Cited

U.S. PATENT DOCUMENTS

| 5,559,038 | A | 9/1996 | Kolhouse |
| 6,358,996 | B1 | 3/2002 | Alexander |

OTHER PUBLICATIONS

Magera et al. "Methylmalonic acid measured in plasma and urine by stable-isotope dilution and electrospray tandem mass spectrometry", Clin. Chem., 2000, v. 46, No. 11, pp. 1804-1810.*

Hušek, "Chloroformates in gas chromatography as general purpose derivatization agents", J. Chromat. B, 1998, v. 717, pp. 57-91.*

Jen Pietzsch et al. Rapid determination of total promocysteine in human plasma by using N(O.5) Ethoxycarbonyl ethyl ester derivatives and GC-MS. Clinical Chemistry, 1997, p. 2001-2004, vol. 43(10).

Petr Husek and Petr Simek. Advances in amino acid analysis. LCGC Sep. 2001, p. 986-999, vol. 19.

Ping Cao and Mehdi Moini. Quantitative analysis of fluorinated ethylchlosofosmate derivatives of protein amino acids and hydrolysis products of small peptides using chemical ionization GC-MS. J. of Chromatography A, 1997, p. 111-117 vol. 759.

William A. Joern. Unexpected volatility of barbiturate derivatives: an extractive alkylation procedure for barbiturates and benzoylecgonine. Journal of Analytical Toxicology, Nov. 1994, p. 423, vol. 18.

* cited by examiner

*Primary Examiner*—Yelena G Gakh

(57) ABSTRACT

Method of identification and quantitative analysis of carboxylic acid(s) in a sample by mass spectrometry using stable isotope labeled internal standard is provided. Said internal standard is prepared by reaction of an authentic sample of said carboxylic acid with a stable isotope labeled reagent, and is added to a sample containing said carboxylic acid. Said carboxylic acid in said sample is then quantitatively converted to a chemical compound of identical structure, except the stable isotope atoms, as that of said internal standard using a non-labeled reagent. Said sample is then extracted and the extract is analyzed by mass spectrometry. Identification and quantification of said carboxylic acid are made from a plot of ion ratio of said converted carboxylic acid to said internal standard versus carboxylic acid concentration.

17 Claims, 1 Drawing Sheet

Mass spectrum of the synthesized ketoprofen ethyl ester-d5 in molecular ion mode.

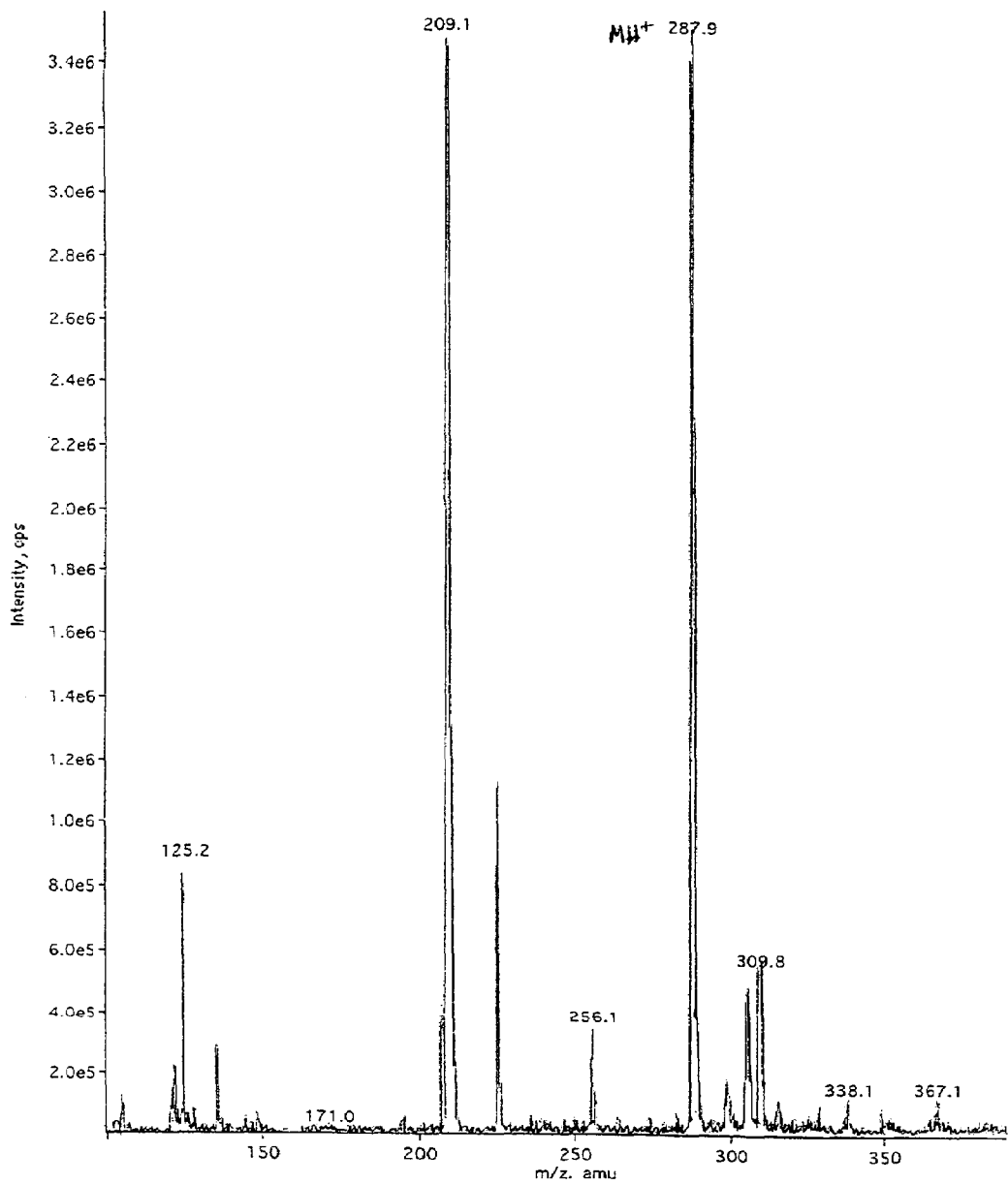
Figure 1: Mass spectrum of the synthesized ketoprofen ethyl ester-d5 in molecular ion mode.

METHOD OF QUANTIFICATION OF CARBOXYLIC ACIDS BY MASS SPECTROMETRY

CROSS-REFERENCE TO RELATED APPLICATIONS

Not applicable

STATEMENT REGARDING FEDERALLY SPONSORED RESEARCH OR DEVELOPMENT

Not applicable

BACKGROUND OF THE INVENTION

This invention pertains to methods of quantitative analysis of carboxylic acids in a sample by isotope dilution mass spectrometry. The stable isotope labeled esters are used as internal standards. The sample may be a biological fluid, such as serum, urine etc., or an aqueous sample such as an environmental or an agricultural sample.

While various methods of analysis such as immunoassays and chromatographic analysis—LC (liquid chromatography), GC (gas chromatography), and TLC (thin layer chromatography)—have been reported for identification and determination of levels of carboxylic acids in analytical samples, the absolute and unequivocal identification and quantitative analysis of those compounds are combinations of chromatographic analysis and MS (mass spectrometry) such as GC-MS and LC-MS. The accuracy and precision of these methods are usually the highest when stable isotope analogs of the analytes are used as internal standards.

The mass spectrometry method of analysis using stable isotope internal standards is commonly called isotope dilution mass spectrometry. This method takes advantage of the similar chemical and physical behaviors of analytes and their respective isotope labeled internal standards towards all phases of sample preparation and also towards instrument responses. It uses the mass differentiation between analytes and their respective internal standard in mass spectrometry for quantification. The requirement for this method of analysis is the availability of stable isotope labeled internal standards.

The commonly used stable isotope labeled internal standard of an analyte is a chemical compound that has the same chemical structure as that of the analyte except that one or more substituent atoms are stable isotopes. Four commonly used stable isotopes are deuterium, carbon-13, nitrogen-15, and oxygen-18. For every hydrogen atom that is replaced by a deuterium atom, the molecular weight of resulting chemical compound is increased by one mass unit. This is also true for replacing a carbon atom with a carbon-13 atom, or by replacing a nitrogen atom with a nitrogen-15 atom. In the case of replacing an oxygen atom with an oxygen-18 atom, the molecular increase is two mass units. Although the acceptable stable isotope labeled internal standard for isotope dilution mass spectrometry method is the one that is not contaminated with any of the unlabeled material, the ideal one should be the one with the highest isotopic purity and contains as many stable isotope atoms as possible. The ideal one, however, must not contain any labeled isotope that can be exchanged for the unlabeled isotope under particular sample preparation conditions.

These criteria of an ideal stable isotope labeled internal standard present a challenge for organic synthesis chemists who help the analytical chemists in the analysis. Most often the synthesis of stable isotope internal standards is not simply an isotope exchange reaction. Easily exchangeable atoms are usually due to possible re-exchange during sample preparation steps. Organic chemists often have to carry out multi-step synthesis to make stable isotope labeled internal standards. Even though many stable isotope labeled reagents are commercially available, the choice of appropriate labeled reagent for chemical synthesis of stable isotope labeled internal standards is still very limited. The limited isotope labeled reagents and the multi-step synthesis contribute to the high cost of synthesis of stable isotope internal standards. Even if the analytical chemist who carries out the analysis can afford the cost of the synthesis, there is also a time factor that he or she has to consider before ordering the synthesis. Situations where organic chemists spent weeks and months on a synthesis project and came up with nothing at the end were common. This invention offers a solution for this problem.

The objective is a short and reliable method of preparing a stable isotope labeled internal standard that is suitable for the MS analysis of an analyte in question, but not the synthesis of the stable isotope labeled analyte. Within the context of the isotope dilution mass spectrometry method, both analyte and its internal standard have to have identical chemical structures, with the exception of the isotope atoms which provide the mass differentiation upon mass spectrometric analysis. Analytical chemists who uses GC-MS for their analysis often "derivatize" the analyte and its stable isotope labeled analyte (used as internal standard) into chemical compounds that can easily pass through the GC column or else provide better instrumental responses. The analysis becomes the analysis of the "derivatized" analyte and the "derivatized" internal standard, but still provides comparably accurate results of concentrations of the analyte itself. Examples of these analyses are found in cited references. Using similar reasoning, one can synthesize a stable isotope derivative of the analyte by reacting it with a stable isotope labeled reagent. The resulting isotope labeled chemical compound can be used as internal standard in the analysis of the analyte, providing that the analyte in the analyzed sample will be converted to a chemical compound of identical structure as that of the internal standard using a non-labeled reagent. There are 3 requirements for the usefulness of this method:

1. The analyte in the sample must be quantitatively converted to the compound of identical structure (except the labeled atoms) as that of the added isotope labeled internal standard using a non-labeled reagent.
2. Absolutely no conversion of the isotope labeled internal standard to the non-labeled compound because the conversion of the analyte happens in the sample in the presence of the added isotope labeled internal standard.
3. The conversion of the analyte into the compound of identical structure as that of the added isotope labeled internal standard has to be accomplished before any isolation method i.e. extraction, is performed.

The first two requirements relate to the chemistry of the analyte in question. The efficiency of a chosen chemical reaction depends on the type of reaction which, in turn, depends on the type of functional groups of the analyte. This invented method relates to the analysis of carboxylic acids whose chemistry focus on the reactivity of the carboxyl functional groups of the analyte.

Quantitative reactions of carboxylic acids in aqueous samples are:
1. Conversion to an ester using a chloroformate and an alcohol.
2. Conversion to an ester using an alkyl halide under alkaline conditions.

There are other reactions of carboxylic acids that are very efficient, but the above conversion reactions are very efficient in aqueous environment and can be performed at room temperature and in a relatively short reaction time. These are necessary and practical features for routine analysis of carboxylic acids in aqueous samples.

BRIEF SUMMARY OF THE INVENTION

The current invention provides for a method of identification and quantification of carboxylic acid in a sample by isotope dilution mass spectrometry. The stable isotope labeled internal standard of said carboxylic acid is synthesized beforehand by reacting a sample containing said analyzed carboxylic acid with a labeled reagent. Following this step, said stable isotope labeled internal standard is then added to said sample containing said analyzed carboxylic acid. Said analyzed carboxylic acid is then converted to a non labeled analog of said labeled internal standard with identical chemical structure as said labeled internal standard except for the stable isotope atoms using a non-labeled reagent. Both said converted carboxylic acid and its corresponding stable isotope labeled internal standard are then extracted and analyzed by mass spectrometry. Said stable isotope labeled internal standard provided in the current invention are labeled carboxylic acid ester analogs of said analyzed carboxylic acid. There are 2 methods to quantitatively convert a carboxylic acid to a carboxylic acid esters under aqueous conditions. One method requires a chloroformate to activate the acid to form an intermediate activated ester which reacts with an added alcohol to form the desired carboxylic acid ester. The other method requires to strong alkaline condition for the carboxylic acid to react with an added alkyl halide to form the desired carboxylic acid ester.

In comparison with the traditional method of isotope dilution mass spectrometric analysis of more than one carboxylic acids, the invented method offers the following advantages:

1. The efficiency and simplicity of the above reactions makes possible the short, reliable, and quick synthesis of individual stable isotope labeled internal standards, whereas in the traditional method of analysis, stable isotope labeled internal standard of each carboxylic acid has to be independently synthesized.
2. It is possible to quickly and efficiently synthesize a library of stable isotope internal standards for the analysis of an entire library of carboxylic acids using these reactions and only one commercially available stable isotope labeled reagent.
3. Because the synthesis of stable isotope labeled internal standard in this invented method is usually a one-step synthesis, the entire process of synthesis and sample preparation can be performed in an automated fashion. The internal standard is prepared in one step, excess isotope reagent is then destroyed or removed, and the prepared internal standard can be added directly to the samples without purification. The non-labeled reagent is added and the sample is ready for extraction shortly thereafter.

These attractive features make the method suitable for high throughput analysis of carboxylic acids by isotope dilution mass spectrometry.

BRIEF DESCRIPTION OF THE DRAWINGS

FIG. 1 illustrates a mass spectrum of the synthesized ketoprofen ethyl ester-d5 in molecular ion mode.

DETAILED DESCRIPTION OF THE INVENTION

The current invention provides for a method of identification and quantification of carboxylic acid(s) in a sample by mass spectrometry. Said carboxylic acid(s) has the following formulas $R_1COOH$ wherein $R_1$ is alkyl, aryl, heteroatom containing, cyclic or non-cyclic groups. The current method comprises, as an intergral part of said analysis of said carboxylic acid(s), the following steps:

1. Synthesizing labeled carboxylic acid ester internal standard(s) by reacting an authentic sample of said carboxylic acid(s) with a stable isotope labeled reagent to form said carboxylic acid ester internal standard(s) of the general formulas $R_1COOR_2$, wherein $R_2$ is a stable isotope labeled alkyl group. Said $R_2$ stable isotope labeled alkyl group is selected from the group consisting of $CD_3$ or $CD_2CD_3$ or $CD_2C_6D_5$. Depending on the method mentioned above to convert a carboxylic acid to a carboxylic acid ester, said stable isotope labeled derivatizing reagent is either a chloroformate and a labeled alcohol selected from the group consisting of labeled methanol and labeled ethanol, or a base and a labeled alkyl halide selected from the group consisting of labeled methyl iodide, labeled ethyl iodide, and labeled benzyl chloride.
2. A known amount of said stable isotope labeled ester internal standard(s) was then added to said sample containing said carboxylic acid(s) to be analyzed.
3. Said sample was then contacted with either a chloroformate such as isobutylchloroformate and a non-labeled alcohol selected from a group consisting of methanol and ethanol, or a strong base such as sodium hydroxide and an alkyl halide selected from a group consisting of methyl iodide, ethyl iodide, and benzyl chloride, to quantitatively convert said carboxylic acid(s) in said sample into said carboxylic acid ester(s) of identical structure as that of said carboxylic acid ester internal standard(s) except for the stable isotope atoms.

EXAMPLE

Analysis of Ketoprofen in Human Plasma

Step 1: Preparation of Ketoprtofen Ethyl Ester-d5.

A solution of 25 mg of ketoprofen in 0.5 ml tetrahydrofuran was treated with 2 equivalents of ethanol-d5 and one equivalent dicyclohexyl carbodiimide. The resulting solution was stirred for 20 hours then was quenched with water. The aqueous phase was extracted with ethyl acetate and the combined organic phases were dried with magnesium sulfate. The filtered solution was concentrated and the residue was purified by column chromatography using silica gel as absorbant and hexane ethyl acetate mixture as eluant. The fractions containing clean ketoprofen ethyl ester-d5 were combined and concentrated to give 8 mg product as a white solid. MS analysis gave MH+ 288.

Step 2: Preparation of Working Standard Solutions and Internal Standard Solution.

Working standard solutions of ketoprofen were prepared by weighing ketoprofen and diluting the stock solution to appropriate concentration as follows:

| Solution | A | 0.1 ug/ml in ethyl acetate |
|---|---|---|
|  | B | 0.2 ug/ml |
|  | C | 0.5 ug/ml |
|  | D | 2.0 ug/ml |
|  | E | 5.0 ug/ml |
|  | F | 15.0 ug/ml |
|  | G | 20.0 ug/ml |

Working quality control standard solutions of ketoprofen were prepared by independently weighing ketoprofen and diluting the stock solution to appropriate concentration as follows:

| QC Solution | J | 0.3 ug/ml in ethyl acetate |
|---|---|---|
|  | K | 6.0 ug/ml |
|  | L | 14.0 ug/ml |

Working internal standard solution of ketoprofen were prepared by weighing ketoprofen ethyl ester-d5 and diluting the stock solution to a working concentration of 10 ug/ml in ethyl acetate.

Step 3: Preparation of Calibration Samples and Quality Control Samples in Human Plasma.

Ketoprofen-free human plasma aliquots of 0.1 ml were treated with 100 ul of solution A to G to make calibration samples A to G.

Ketoprofen-free human plasma aliquots of 0.1 ml were treated with 100 ul of solution J to L to make quality control samples J to L.

Both calibration samples and quality control samples were then treated with 100 ul of the internal standard working solution.

A human plasma aliquot of 0.1 ml was treated with 100 ul of the internal standard solution to make the "zero" sample.

Another human plasma aliquot of 0.1 ml was not treated with 100 ul of the internal standard solution to make the "blank" sample.

Step 4: Ester Formation and Extraction.

To all prepared samples were added 100 ul of a solution of water:ethanol:pyridine (60:32:8) followed by 10 ul of ethyl chloroformate. The samples were mixed and left standing at room temperature for 15 minutes. Aqueous 1N hydrochloric acid, 0.5 ml, was added to each sample and they were extracted with 0.5 ml ethyl acetate. Each extract was separated and concentrated. The residue of each extract was reconstituted with 100 ul of acetonitrile.

Step 5: Analysis of Reconstituted Extracts by LC/MS/MS.

A total of 12 reconstituted extracts were loaded on a Perkin Elmer autosampler that was connected to a Perkin Elmer LC pump and a PE Sciex API 365 MS. Each extract was run through an Inersil column of 5 um at a rate of 0.5 ml/min of acetonitrile/water 50/50 mixture. The eluate was directly fed to the MS ion source. MS data were collected for 1.5 min per injection.

MS analysis was performed in MRM mode. m/z 283.0>m/z 209.0 was monitored for ketoprofen ethyl ester while m/z 288.0>m/z 209.0 was monitored for ketoprofen ethly ester-d5. Collected data were ploted against concentration using McQuan 1.5 software.

Results are tabulated as follows:

Ketoprofen

Internal Standard: is

Weighted (1/x*x)

Intercept=0.030

Slope=0.040

Correlation Coeff.=0.996

Use Area

| Filename | Accuracy | Conc. | Calc. Conc. | Int. Ratio |
|---|---|---|---|---|
| Keto A Standard | 93.212 | 0.100 | 0.093 | 0.034 |
| Keto B Standard | 108.585 | 0.200 | 0.217 | 0.039 |
| Keto C Standard | 114.109 | 0.500 | 0.571 | 0.053 |
| Keto D Standard | 95.505 | 2.000 | 1.910 | 0.107 |
| Keto E Standard | 97.619 | 5.000 | 4.881 | 0.225 |
| Keto F Standard | 94.386 | 15.000 | 14.158 | 0.596 |
| Keto G Standard | 96.583 | 20.000 | 19.317 | 0.802 |
| Keto J QC | 104.298 | 0.300 | 0.313 | 0.043 |
| Keto K QC | 98.680 | 6.000 | 5.921 | 0.267 |
| Keto L QC | 100.604 | 14.000 | 14.085 | 0.593 |

REFERENCES

| U.S. patent documents | | |
|---|---|---|
| 5,559,038 | Sep. 24, 1996 | J. Fred Kolhouse |
| 6,358,996 | Mar. 19, 2002 | Michael S. Alexander |

Other References

Petr Husek, "Chloroformates in gas chromatography as general purpose derivatizing agents", Journal of Chromatography B, 1998, page 57-91, vol. 717.

Jens Pietzsch et al, "Rapid determination of total homocysteine in human plasma by using N(O,S)-Ethoxycarbonyl ethyl ester derivatives and gas chromatography-mass spectrometry", Clinical Chemistry, 1997, page 2001-2004, vol. 43(10).

Petr Husek and Petr Simek, "Advances in amino acid analysis", LCGC Sept. 2001, page 986-999, vol. 19.

Ping Cao and Mehdi Moini, "Quantitative analysis of fluorinated ethylchloroformate derivatives of protein amino acids and hydrolysis products of small peptides using chemical ionization gas chromatography-mass spectrometry", Journal of Chromatography A, 1997, page 111-117, vol. 759.

William A. Joern, "Unexpected volatility of barbiturate derivatives: an extractive alkylation procedure for barbiturates and benzoylecgonine", Journal of Analytical Toxicology, Nov. 1994 page 423, vol. 18.

We claim:

1. A method of one step synthesis of stable isotope labeled internal standards and derivatizing reaction for the purpose of quantification of a carboxylic acid in an aqueous sample comprising the steps of:
   a) synthesizing labeled said carboxylic acid ester for use as labeled internal standard by reaction of an authentic sample of carboxylic acid with a labeled derivatizing reagent having at least one stable isotope atom;

b) combining a known amount of said labeled carboxylic acid ester internal standard with said aqueous sample comprising said carboxylic acid;

c) contacting said resulting sample with a non labeled version of said labeled derivatizing reagent under basic conditions to convert said carboxylic acid in said aqueous sample into a carboxylic acid ester of identical structure as that of said carboxylic acid ester internal standard with the exception of the stable isotope atoms;

d) extracting said sample to isolate said carboxylic acid ester and said labeled carboxylic acid ester internal standard; and e) quantifying said carboxylic acid ester using said labeled carboxylic acid ester internal standard by mass spectrometry to determine the concentration of said carboxylic acid in said sample.

2. The method of claim 1 wherein said carboxylic acid is a small molecular weight (less than 1000 atomic mass unit) carboxylic acid having the chemical formulas $R_1COOH$ wherein $R_1$ is alkyl group or aryl group or heteroatom containing group or cyclic group or non-cyclic group.

3. The method of claim 1 wherein said labeled carboxylic acid ester is a small molecular weight (less than 1000 atomic mass unit) carboxylic acid ester having the chemical formulas $R_1COO R_2$ wherein $R_1$ is alkyl group or aryl group or heteroatom containing group or cyclic group or non-cyclic group and $R_2$ is a labeled alkyl group having at least one stable isotope atom.

4. The method of claim 1 wherein said labeled derivatizing reagent is a labeled alcohol $R_2OH$ wherein $R_2$ is a labeled alkyl group having at least one stable isotope atom and said non labeled derivatizing reagent is the same alcohol $R_2OH$ except that $R_2$ contains no stable isotope atom and the derivatization reaction is performed in the presence of a chloroformate and a base.

5. The method of claim 4 wherein said stable isotope labeled alkyl group $R_2$ is $CD_3$ wherein said carboxylic acid is reacted with a chloroformate and a labeled methanol, or with a base and a labeled methyl iodide.

6. The method of claim 4 wherein said stable isotope labeled alkyl group $R_2$ includes $CD_3$, $CD_2CD_3$, and $CD_2C_6D_5$.

7. The method of claim 4 wherein said stable isotope labeled alkyl group $R_2$ is $CD_2C_6D_5$ wherein said carboxylic acid is reacted with a base and a labeled benzyl chloride.

8. The method of claim 4 wherein said non labeled alcohol $R_2OH$ is selected from a group consisting of methanol, benzyl alcohol, and ethanol.

9. The method of claim 4 wherein said chloroformate is selected from a group consisting of isobutyl chloroformate, methyl chloroformate, and ethyl chloroformate.

10. The method of claim 4 wherein said base is selected from a group consisting of sodium hydroxide, sodium carbonate, pyridine and triethylamine.

11. The method of claim 1 wherein said extraction step d) can be any appropriate separating methods such as solid phase extraction, liquid-liquid extraction or solid supported liquid-liquid extraction.

12. The method of claim 1 wherein said alkyl halide is selected from a group consisting of methyl iodide, ethyl iodide, and benzyl chloride.

13. The method of claim 1 wherein said sample contains either a singularity or a plurality of carboxylic acids.

14. The method of claim 1 wherein more than one carboxylic acids in said sample can be converted to carboxylic acid esters using a single derivatizing reagent.

15. The method of claim 1 wherein more than one labeled carboxylic acid ester internal standards can be synthesized using a single labeled derivatizing reagent.

16. The method of claim 1 wherein said additional reaction step c) is performed in an aqueous environment.

17. The method of claim 1 wherein said stable isotope atom is selected from a group consisting of deuterium, carbon-13, nitrogen-15, and oxygen-18.

* * * * *